United States Patent [19]

Favonio

[11] 4,358,971
[45] Nov. 16, 1982

[54] DENTIST'S DRILL CHUCK

[76] Inventor: Osvaldo Favonio, Via per Bellusco 17, Ornago (Milan), Italy

[21] Appl. No.: 206,381

[22] Filed: Nov. 12, 1980

[30] Foreign Application Priority Data

Nov. 13, 1979 [IT] Italy .............................. 23110/79[U]

[51] Int. Cl.³ ............................................. B25B 17/00
[52] U.S. Cl. ........................................................ 81/55
[58] Field of Search ..................... 81/55; 433/166, 135, 433/116; 51/378, 168

[56] References Cited

U.S. PATENT DOCUMENTS

| | | | |
|---|---|---|---|
| 1,260,698 | 3/1918 | Moore et al. | 81/55 |
| 1,350,002 | 8/1920 | Burleu | 433/142 |
| 1,426,682 | 8/1922 | Snell | 81/55 |
| 2,696,700 | 12/1954 | Tocci | 51/378 |
| 2,757,455 | 8/1956 | Birnbaum | 433/135 |
| 4,193,327 | 3/1980 | Lares et al. | 81/55 |

Primary Examiner—James L. Jones, Jr.
Attorney, Agent, or Firm—Oblon, Fisher, Spivak, McClelland & Maier

[57] ABSTRACT

An utensil for mounting a tool on the chuck of a dentist's drill and for removing the tool for replacement is provided, which consists of a U-shaped frame, one web of which supports a rotatable and axially shiftable spring biased wrench section, the other web carrying a chuck-clamping array of projections and a resting reference plane, the wrench section engaging a correspondingly headed screw which fastens a drill tool to the drill shank and releases the tool when the screw is released.

1 Claim, 4 Drawing Figures

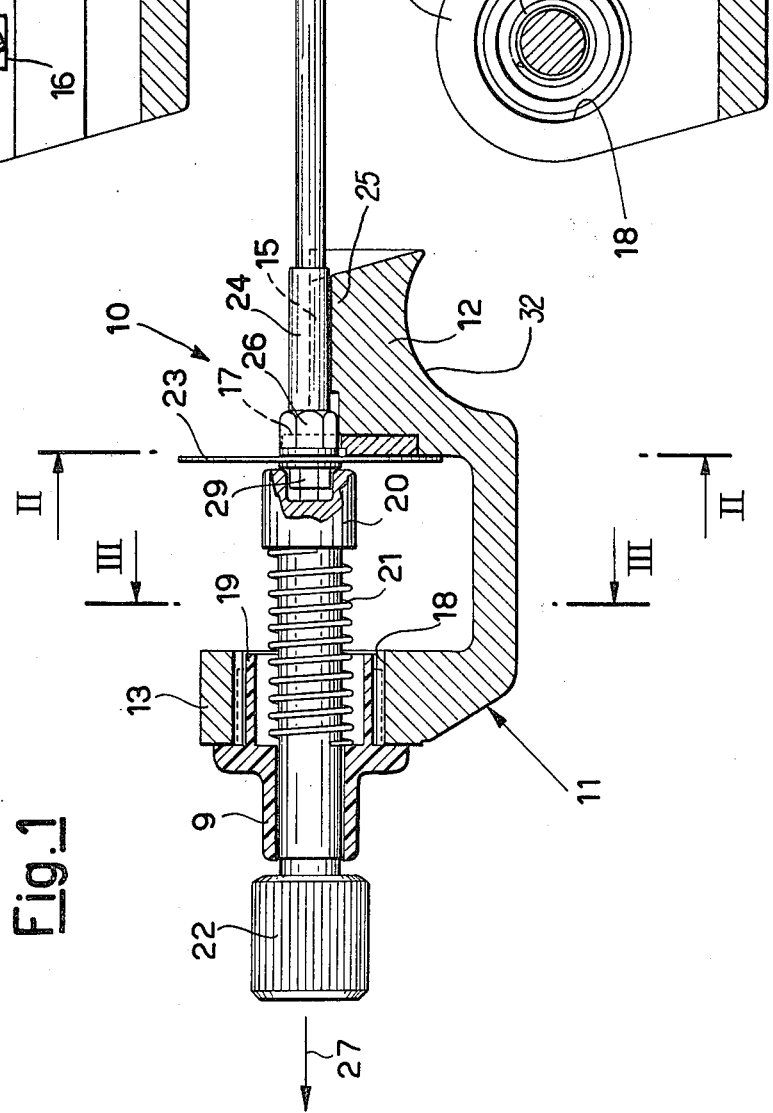

DENTIST'S DRILL CHUCK

As is well known to those who are skilled in this particular art, tools for dentistry use, such as abrasive discs, grinding wheels, mills and others, must be secured in a removable manner to a chuck which, in its turn, is intended to be fastened to a drill handle.

This fastening has been embodied heretofore by a screw which is passed through a central bore of the tool and is screwed to a tapped end section of the chuck. The screw is manipulated by a small screw-driver the blade of which is inserted into a diametrical slit of the screw head.

Such a fastening system, due to the small dimensions of the component parts involved, is lengthy, inconvenient to a degree and also hazardous, both when installing the tool and removing it in and from the chuck.

As a matter of fact, the chuck must be held with the pliers or another like tool grasped with either hand, whereas the other hand manipulates a screw driver for acting upon the head of the set screw for fastening the tool to the chuck. It is thus apparent that the screw-driver, under a thrust which is not exactly axially directed, may be cleared from the screw head slit and hurt the operators' hand which holds the chuck.

An object of the present invention is to do away with the shortcomings enumerated above and, having this object in view, according to the invention, it has been envisaged to provide a tool-carrier chuck, for dentistry use, of the kind comprising an internally tapped end section, to which a tool is secured by a screw, characterized in that said tapped section is terminated by an external polygonal head adapted stably to be engaged in the complementary seat of a tool which serves to screw said screw into said tapped section.

Preferably, the screw has a polygonally shaped head and the tool is of the bush-type wrench.

The wrench may comprise a substantially U-shaped supporting member between the prongs of which there extends a bushing which can be rotated and translated axially against the bias of a spring, the wrench being carried by a prong of the supporting member, whereas the opposite prong has a seat, coaxial with the wrench, in the interior of which the chuck can be engaged, to which the drill tool is fastened by a polygonal-head screw matching the bush wrench, the tool being thus clamped between the wrench and the supporting member prong.

Preferably, the wrench is mounted within an overhanging portion of a bushing which is inserted into a bore formed through the prong, the wrench extending beyond said overhanging portion with a knurled knob away of the bushing.

Still more preferably, said seating is formed on a resting plane of the prong and has a channeled shape which is terminated by a U-shaped section placed between a couple of confrontingly positioned shoulders, the polygonal header of the tool-carrying chuck being engageable by said shoulders.

The structural and operative features of the invention and its advantages will become still more clearly understandable from the ensuing description of an exemplary embodiment, aided by the accompanying drawings, wherein:

FIG. 1 is a lengthwise cross-sectional view showing and assembly according to the invention in its working position.

FIG. 2 is a cross-sectional view taken along the line II—II of FIG. 1.

FIG. 3 is a cross-sectional view taken along the line III—III of FIG. 1, and

Figure 4:
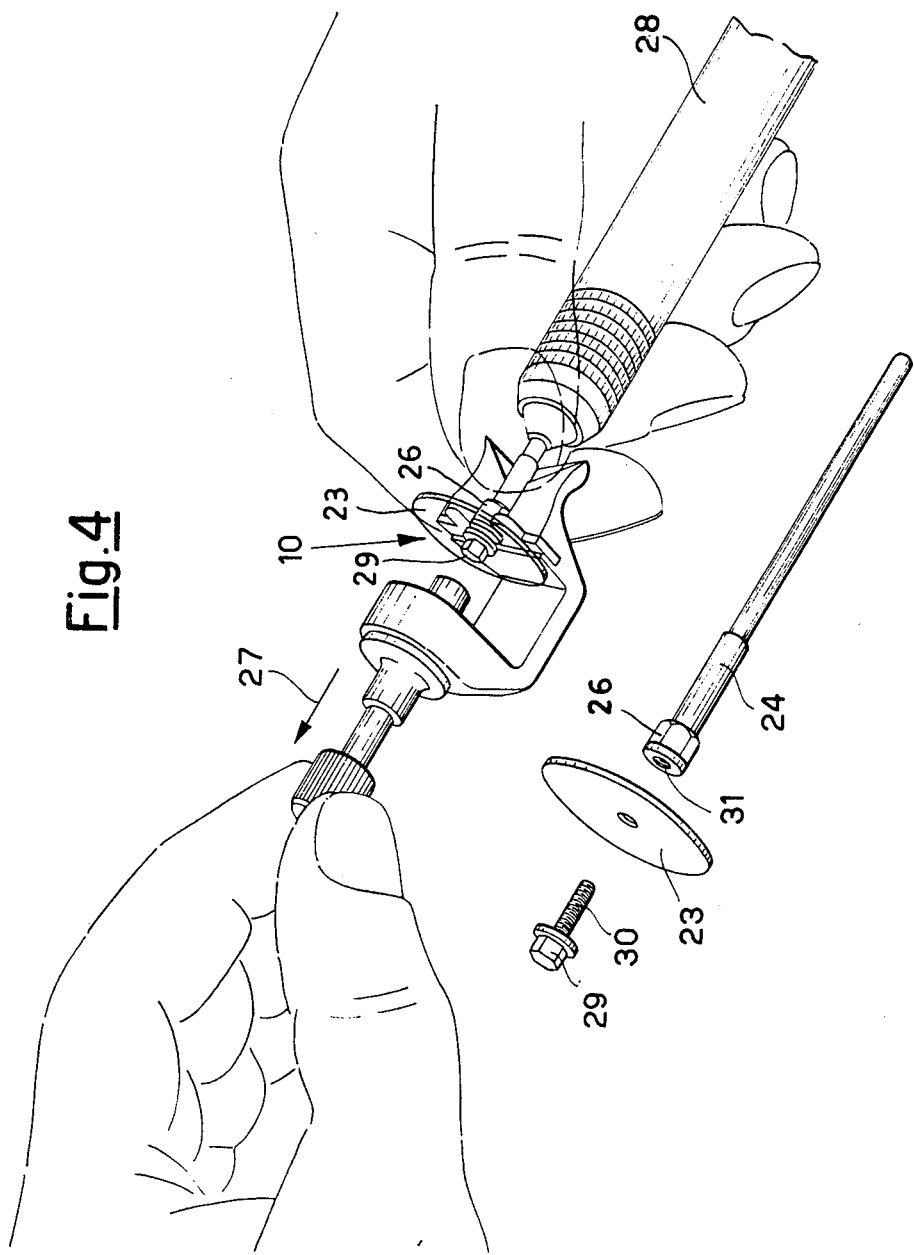
FIG. 4 is a perspective exploded view.

With reference to the drawings, the assembly in question is generally indicated at 10 and is structurally comprised of a supporting member in the shape of a U.

The prong 12 of the supporting member 11 is shorter than the confronting prong 13 and has a resting plane 14. On the plane 14 there is formed a gutter like seat 15 which is terminated by a "U" section 16 placed between a couple of retaining shoulders 17.

The prong 13 has a bore 18 into which a bushing 19 is inserted: in an overhanging portion 9 of 19, a chambered wrench section 20 is mounted for rotation and can axially be translated against the bias of a spring 21. The opposite position relative to the bushing 20 shows a knurled manipulating knob 22.

The tool described above is employed as follows in combination with the polygonal head (26) chuck 24 made according to the invention.

The drill-tool, for example, an abrasive disc 23 (a so-called tooth-separator) is placed resting with its chuck 24 within the seat 15 and with the disc 23 abutting the planar abutting surface 25 of the supporting member 11. By so doing, the polygonal head 26 of the chuck 24 is clamped between the shoulders 17 and the U-shaped section 16 (FIG. 2). Thus, the rotation of the drill-tool about its own axis is prevented. It is to be noted that the operation aforesaid is made by manually displacing the wrench 20 in the direction of the arrow 27, as shown in FIG. 4, wherein the tool is depicted as applied to a drill handle 28.

As the manual pull is discontinued, the spring 21 biases the bushing 20 to engage the polygonal head 29 of the bolt 30, which secures the disc 23 to the tapped section 31 of the shank 24. In this connection, the mutual positions of the bore 18 and the seat 15 are so calculated as to have the bushing 20 and the header 29 coaxial with one another.

By rotating the wrench 20 it is now possible easily to unscrew the screw 30 and to remove the disc 23 for replacement.

Obviously, the same operations described above can be carried out to screw onto the chuck another drill tool.

The supporting member 11, in addition, has a groove 32 to facilitate grasping (FIG. 1).

The objects of the invention have thus been achieved both simply and functionally.

I claim:

1. In a combination of a chuck of the kind having a tapped end section to which a dentistry drill tool is to be fastened by a screw and a utensil for screwing said screw into said tapped end section, the improvement comprising:
    said tapped section of said chuck terminated by an external polygonal head adapted to be engaged stably by a complementary seat of said utensil;
    said screw having a polygonal head;
    said utensil having a pipe wrench section and a substantially U-shaped supporting member defining opposed prongs between which there extends said pipe wrench section rotatable and axially translatable against the bias of a spring, said wrench section being borne by a selected prong of said supporting member whereas the opposite prong has a seat coaxial with the wrench section within which seat the chuck can be engaged, said screw having a polygonal head matching the wrench section, a drill tool being fastened to said chuck by said polygonal head screw by means of operation of the pipe wrench section, the drill tool being thus clamped between the wrench section and the prong of the supporting member;

said selected prong having a bore formed therethrough and a bushing mounted in said bore, said bushing having an overhanging portion in which said wrench section is mounted, the wrench section extending beyond said overhanging portion by a knob opposite to the wrench section chamber;

said seat of said opposite prong formed on a resting plane thereof, said resting plane having a gutter-like shape and terminating with a U-section placed between a couple of confronting shoulders, said U-section and said shoulders engaging the polygonal head of the drill tool chuck; and said opposite prong having a planar abutting surface disposed apart from said seat and exterior of said prongs, said planar abutting surface provided as a support to maintain planar alignment of said chuck with said screw and said wrench section.

* * * * *